US005681300A

United States Patent [19]
Ahr et al.

[11] Patent Number: 5,681,300
[45] Date of Patent: Oct. 28, 1997

[54] ABSORBENT ARTICLE HAVING BLENDED ABSORBENT CORE

[75] Inventors: Nicholas Albert Ahr; John Richard Noel; Thomas Ward Osborn, III, all of Cincinnati, Ohio

[73] Assignee: The Procter & Gamble Company, Cincinnati, Ohio

[21] Appl. No.: 562,709

[22] Filed: Nov. 27, 1995

Related U.S. Application Data

[63] Continuation of Ser. No. 406,753, Mar. 10, 1995, abandoned, which is a continuation of Ser. No. 303,562, Sep. 9, 1994, abandoned, which is a continuation of Ser. No. 966,240, Oct. 26, 1992, abandoned, which is a continuation-in-part of Ser. No. 810,774, Dec. 17, 1991, abandoned, Ser. No. 874,871, Apr. 28, 1992, abandoned, Ser. No. 874,872, Apr. 28, 1992, abandoned, Ser. No. 882,738, May 14, 1992, abandoned, Ser. No. 915,133, Jul. 23, 1992, abandoned, Ser. No. 915,134, Jul. 23, 1992, abandoned, Ser. No. 915,201, Jul. 23, 1992, abandoned, Ser. No. 915,202, Jul. 23, 1992, abandoned, Ser. No. 915,285, Jul. 23, 1992, abandoned, Ser. No. 931,122, Aug. 17, 1992, Pat. No. 5,304,161, Ser. No. 944,764, Sep. 14, 1992, abandoned, Ser. No. 957,575, Oct. 7, 1992, Pat. No. 5,591,149, Ser. No. 926,183, Aug. 7, 1992, abandoned, and Ser. No. 911, Jan. 6, 1993, Pat. No. 5,300,054.

[51] Int. Cl.$^6$ .............................. A61F 13/15; A61F 13/20
[52] U.S. Cl. ..................... 604/367; 604/358; 604/366; 604/370; 604/379; 604/384
[58] Field of Search .......................... 604/358, 366–368, 604/374–379, 384

[56] References Cited

U.S. PATENT DOCUMENTS

| | | |
|---|---|---|
| D. 253,425 | 11/1979 | Roeder. |
| D. 253,550 | 11/1979 | Roeder. |
| 2,787,271 | 4/1957 | Clark. |
| 3,285,245 | 11/1966 | Eldredge et al.. |
| 3,292,619 | 12/1966 | Egler. |
| 3,545,441 | 12/1970 | Gravdahl. |

(List continued on next page.)

FOREIGN PATENT DOCUMENTS

| | | |
|---|---|---|
| 0 040 084 | 11/1981 | European Pat. Off.. |
| 0 080 382 A2 | 6/1983 | European Pat. Off.. |
| 0 088 533 A2 | 9/1983 | European Pat. Off.. |
| 0 156 649 | 10/1985 | European Pat. Off.. |
| 0 159 630 A2 | 10/1985 | European Pat. Off.. |
| 0 172 035 | 2/1986 | European Pat. Off.. |
| 0 201 087 | 11/1986 | European Pat. Off.. |
| 0 294 137 A1 | 12/1988 | European Pat. Off.. |
| 0 343 940 A2 | 11/1989 | European Pat. Off.. |
| 0 359 502 A2 | 3/1990 | European Pat. Off.. |
| 0 474 123 A1 | 3/1992 | European Pat. Off.. |
| 0 518 291 A1 | 12/1992 | European Pat. Off.. |
| 0 518 340 A1 | 12/1992 | European Pat. Off.. |
| 40 24 053 | 1/1992 | Germany. |
| 2 089 214 | 6/1982 | United Kingdom. |
| 2 194 265 | 3/1988 | United Kingdom .............. E04D 3/35 |
| 2197206 | 5/1988 | United Kingdom ................... 604/379 |
| WO 91/15367 | 10/1991 | WIPO ........................... B32B 31/08 |

(List continued on next page.)

Primary Examiner—John G. Weiss
Assistant Examiner—P. Zuttarelli
Attorney, Agent, or Firm—Theodore P. Cummings; Kevin C. Johnson; Jacobus C. Rasser

[57] ABSTRACT

An absorbent article, such as a diaper, sanitary napkin, adult incontinent device which have absorbent cores comprised of blends of different types of fibers are provided. The absorbent articles preferably comprise a liquid pervious topsheet, a liquid impervious backsheet joined to the topsheet, a blended absorbent core positioned between the topsheet and the backsheet, and an acquisition layer. The absorbent core comprises a homogeneous blend of fibers comprising a first group of short, low denier, hydrophilic fibers and a second group of longer, higher denier, moisture insensitive synthetic fibers. The first group of fibers is selected from a group comprising natural fibers, synthetic fibers or cross-linked cellulose fibers. The second group of fibers comprises between about 5 and 90% of said absorbent core, by weight. The absorbent core is compressed to a density of at least about 0.09 g/cm$^3$ (1.5 g/in.$^2$).

28 Claims, 4 Drawing Sheets

U.S. PATENT DOCUMENTS

| | | |
|---|---|---|
| 3,680,561 | 8/1972 | Baron .................................... 604/375 |
| 3,768,480 | 10/1973 | Mesek et al. . |
| 3,901,236 | 8/1975 | Assarsson et al. . |
| 3,945,386 | 3/1976 | Anczurowski et al. . |
| 3,965,906 | 6/1976 | Karami . |
| 3,967,623 | 7/1976 | Butterworth et al. . |
| 3,971,373 | 7/1976 | Braun . |
| 3,976,074 | 8/1976 | Fitzgerald et al. . |
| 3,994,299 | 11/1976 | Karami . |
| 4,014,341 | 3/1977 | Karami . |
| 4,027,672 | 6/1977 | Karami . |
| 4,047,531 | 9/1977 | Karami . |
| 4,054,141 | 10/1977 | Schwaiger et al. . |
| 4,077,410 | 3/1978 | Butterworth et al. . |
| 4,082,886 | 4/1978 | Butterworth et al. . |
| 4,118,531 | 10/1978 | Hauser . |
| 4,129,132 | 12/1978 | Butterworth et al. . |
| 4,214,582 | 7/1980 | Patel . |
| 4,219,024 | 8/1980 | Patience et al. . |
| 4,223,677 | 9/1980 | Anderson . |
| 4,285,343 | 8/1981 | McNair . |
| 4,324,247 | 4/1982 | Aziz . |
| 4,342,314 | 8/1982 | Radel et al. . |
| 4,357,939 | 11/1982 | Jackson et al. . |
| 4,392,861 | 7/1983 | Butterworth et al. . |
| 4,397,644 | 8/1983 | Matthews et al. . |
| 4,429,001 | 1/1984 | Kolpin et al. . |
| 4,454,187 | 6/1984 | Flowers et al. . |
| 4,469,734 | 9/1984 | Minto et al. . |
| 4,475,911 | 10/1984 | Gellert . |
| 4,500,315 | 2/1985 | Pieniak et al. . |
| 4,589,076 | 5/1986 | Fujioka . |
| 4,605,402 | 8/1986 | Iskra . |
| 4,610,678 | 9/1986 | Weisman et al. . |
| 4,648,876 | 3/1987 | Becker et al. . |
| 4,650,479 | 3/1987 | Insley . |
| 4,655,757 | 4/1987 | McFarland et al. . |
| 4,659,614 | 4/1987 | Vitale . |
| 4,670,011 | 6/1987 | Mesek . |
| 4,687,478 | 8/1987 | Van Tilburg . |
| 4,690,679 | 9/1987 | Mattingly, III et al. . |
| 4,714,647 | 12/1987 | Shipp, Jr. et al. . |
| 4,724,114 | 2/1988 | McFarland et al. . |
| 4,726,976 | 2/1988 | Karami et al. . |
| 4,752,349 | 6/1988 | Gebel . |
| 4,753,840 | 6/1988 | Van Gompel . |
| 4,755,178 | 7/1988 | Insley et al. . |
| 4,773,903 | 9/1988 | Weisman et al. . |
| 4,780,352 | 10/1988 | Palumbo . |
| 4,781,962 | 11/1988 | Zamarripa et al. . |
| 4,784,972 | 11/1988 | Hatada . |
| 4,786,550 | 11/1988 | McFarland et al. . |
| 4,795,453 | 1/1989 | Wolfe . |
| 4,797,318 | 1/1989 | Brooker et al. . |
| 4,798,603 | 1/1989 | Meyer et al. . |
| 4,806,411 | 2/1989 | Mattingly, III et al. . |
| 4,813,948 | 3/1989 | Insley . |
| 4,823,783 | 4/1989 | Willhite, Jr. et al. . |
| 4,844,965 | 7/1989 | Foxman . |
| 4,865,596 | 9/1989 | Weisman et al. . |
| 4,868,023 | 9/1989 | Wian et al. . |
| 4,886,509 | 12/1989 | Mattsson . |
| 4,908,026 | 3/1990 | Sukiennik et al. . |
| 4,917,697 | 4/1990 | Osborn, III et al. . |
| 4,923,454 | 5/1990 | Seymour et al. . |
| 4,935,022 | 6/1990 | Lash et al. . |
| 4,948,639 | 8/1990 | Brooker et al. . |
| 4,950,264 | 8/1990 | Osborn, III . |
| 4,963,638 | 10/1990 | Pazos et al. . |
| 4,980,226 | 12/1990 | Hellgren et al. . |
| 4,994,037 | 2/1991 | Bernardin . |
| 5,002,814 | 3/1991 | Knack et al. . |
| 5,007,906 | 4/1991 | Osborn, III et al. . |
| 5,009,653 | 4/1991 | Osborn, III . |
| 5,023,124 | 6/1991 | Kobayashi . |
| 5,037,409 | 8/1991 | Chen et al. . |
| 5,078,710 | 1/1992 | Suda et al. . |
| 5,085,914 | 2/1992 | Perdelwitz, Jr. et al. . |
| 5,088,993 | 2/1992 | Gaur . |
| 5,147,343 | 9/1992 | Kellenberger . |
| 5,149,335 | 9/1992 | Kellenberger et al. . |
| 5,151,091 | 9/1992 | Glaug et al. . |
| 5,154,714 | 10/1992 | Nomura et al. . |
| 5,207,970 | 5/1993 | Joseph et al. . |
| 5,231,122 | 7/1993 | Palumbo et al. . |
| 5,232,770 | 8/1993 | Joseph . |
| 5,304,161 | 4/1994 | Noel et al. . |
| 5,316,601 | 5/1994 | Hebbard et al. . |
| 5,324,278 | 6/1994 | Visscher et al. . |
| 5,334,176 | 8/1994 | Buenger et al. . |
| 5,334,177 | 8/1994 | Cohen . |
| 5,360,420 | 11/1994 | Cook et al. . |
| 5,366,450 | 11/1994 | DeGroot . |
| 5,368,918 | 11/1994 | Harada et al. . |
| 5,382,245 | 1/1995 | Thompson et al. . |
| 5,432,000 | 7/1995 | Young, Sr. et al. . |

FOREIGN PATENT DOCUMENTS

| | | |
|---|---|---|
| WO 92/14430 | 9/1992 | WIPO .............................. A61F 13/15 |
| WO 92/18677 | 10/1992 | WIPO . |
| WO 93/07321 | 4/1993 | WIPO . |
| WO 93/07322 | 4/1993 | WIPO . |
| WO 93/07323 | 4/1993 | WIPO . |
| WO 93/07324 | 4/1993 | WIPO . |

ABSORBENT ARTICLE HAVING BLENDED ABSORBENT CORE

CROSS-REFERENCE TO RELATED APPLICATIONS

This application is a continuation of application Ser. No. 08/406,753 filed Mar. 10, 1995, now abandoned; which was a continuation of application Ser. No. 08/303,562 filed Sep. 9, 1994, now abandoned; which was a continuation of application Ser. No. 07/966,240 filed Oct. 26, 1992, now abandoned; which was a continuation-in-part of application Ser. No. 07/810,774 filed Dec. 17, 1991, now abandoned; and application Ser. No. 07/874,871 filed Apr. 28, 1992, now abandoned; and application Ser. No. 07/874,872 filed Apr. 28, 1992, now abandoned; and application Ser. No. 07/882,738 filed May 14, 1992, now abandoned; and application Ser. No. 07/915,133 filed Jul. 23, 1992, now abandoned; and application Ser. No. 07/915,134 filed Jul. 23, 1992, now abandoned; and application Ser. No. 07/915,201 filed Jul. 23, 1992, now abandoned; and application Ser. No. 07/915,202 filed Jul. 23, 1992, now abandoned; and application Ser. No. 07/915,285 filed Jul. 23, 1992, now abandoned; and application Ser. No. 07/931,122 filed Aug. 17, 1992, now U.S. Pat. No. 5,304,161; and application Ser. No. 07/944,764 filed Sep. 14, 1992, now abandoned; and application Ser. No. 07/957,575 filed Oct. 7, 1992, now U.S. Pat. No. 5,591,149; and application Ser. No. 07/926,183 filed Aug. 7, 1992, now abandoned; and application Ser. No. 08/000,911 filed Jan. 6, 1993, now U.S. Pat. No. 5,300,054.

FIELD OF THE INVENTION

The present invention relates to absorbent articles such as diapers, sanitary napkins, adult incontinence devices, and the like which have absorbent cores comprised of blends of different types of fibers.

BACKGROUND OF THE INVENTION

Typically, absorbent articles comprise a liquid pervious material that faces the wearer's body, a liquid impervious material that faces the wearer's clothing, and an absorbent body or absorbent core that is sandwiched between the liquid pervious material and the liquid impervious material. In prior absorbent articles, a material comprising comminuted wood pulp, referred to as airfelt, was used in the absorbent core to absorb the liquids and other exudates deposited on the surface of the absorbent article. One of the disadvantages of using airfelt was that a thick layer of airfelt had to be used to obtain the needed capacity.

Recent attempts to improve the effectiveness of absorbent cores have included distributing particles of absorbent gelling material in the absorbent core. The effectiveness of absorbent cores containing particles of absorbent gelling material often, however, are adversely affected by a phenomenon called "gel blocking". The term "gel blocking" describes a situation that occurs when a particle of absorbent gelling material is wetted and the particle swells. The swelling of a number of such particles inhibits liquid transmission into other portions of the absorbent core. Wetting of the rest of the absorbent core, therefore, takes place via a very slow diffusion process. This may have the effect that the subsequent acquisition of liquid by the absorbent core becomes much slower than the discharge of the liquids to be absorbed. As a result, leakage from the absorbent article may take place well before the particles of absorbent gelling material in the absorbent core are fully saturated or before the liquid can diffuse or wick past the "blocking" particles into the rest of the absorbent core.

Another problem that exists in absorbent articles having absorbent cores comprised of airfelt, with or without absorbent gelling materials, is that such structures tend to collapse when the airfelt becomes wet. When the absorbent material collapses, it may wad up and become hard and inflexible. This can make the absorbent article very uncomfortable to wear.

A number of efforts have been directed to these effects and/or other problems. Some of these efforts are described in U.S. Pat. No. 4,610,678 issued to Weisman, et al. on Sep. 9, 1986; U.S. Pat. No. 4,673,402 issued to Weisman, et al. on Jun. 16, 1987; and European Patent Application EP-A-254,476 assigned to The Procter & Gamble Company, published Jan. 27, 1988, the disclosures of which are incorporated by reference herein.

The first patent listed, U.S. Pat. No. 4,610,678, teaches flexible, high density absorbent structures that comprise a mixture of hydrophilic fibers and particles of absorbent gelling material. The structures are substantially unbonded. (That is, they have a relatively low number of fiber/fiber bonds and fiber/absorbent gelling material particle bonds). This is accomplished by avoiding the exposure of the fibers and hydrogel particles to water or humidity. The structures are compressed to a density of from about 0.15 to about 1 g/cm$^3$. The absence of bonding allows these structures to quickly regain volume upon initial wetting and to more fully exploit the absorbent capacity of absorbent gelling materials.

One attempt to solve the comfort problem is described in U.S. Pat. No. 4,397,644 issued to Matthews, et al. The Matthews, et al. patent discloses the use of a comfort enhancing layer surrounding an absorbent layer. The upper portion of the comfort enhancing layer is referred to as a fluid transfer layer. The fluid transfer layer may contain blends of crimped thermoplastic fibers, non-thermoplastic fibers, absorbent or superabsorbent fibers and cellulosic fibers. However, the principal absorbent layer is a conventional airfelt or cellulosic fiber/airfelt structure.

Several other patents discussing the addition of thermoplastic material to absorbent articles for various purposes include: U.S. Pat. No. 3,285,245 issued to Eldridge, et al.; U.S. Pat. No. 3,545,441 issued to Gravdahl; U.S. Pat. No. 3,976,074 issued to Fitzgerald, et al.; U.S. Pat. No. 4,047,531 issued to Karami; U.S. Pat. No. 4,054,141 issued to Schwaiger, et al.; U.S. Pat. Nos. 4,082,886 and 4,129,132 issued to Butterworth, et al.; U.S. Pat. No. 4,214,582 issued to Patel; and, U.S. Pat. No. 4,219,024 issued to Patience, et al.

The patents describing the use of thermoplastic materials, however, do not disclose absorbent articles which both have absorbent material that has a reduced tendency to collapse when wetted, and which optimizes the use of the core material therein.

Thus, a need exists for absorbent articles with improved absorbent cores which may optionally have particles of absorbent gelling material therein. In particular, a need exists for absorbent articles having absorbent material that has a reduced tendency to collapse when wetted, and optimizes the use of the core material therein.

Therefore, it is an object of the present invention to provide absorbent articles having the characteristics described above.

These and other objects of the present invention will be more readily apparent when considered in reference to the following description and when taken in conjunction with the accompanying drawings.

SUMMARY OF THE INVENTION

In accordance with the present invention, an absorbent article, such as a diaper, a sanitary napkin, or an adult incontinence device, or the like which has an absorbent core comprised of blends of different types of fibers.

The absorbent article preferably comprises a liquid pervious topsheet, a liquid impervious backsheet joined to the topsheet, a blended absorbent core positioned between the topsheet and the backsheet, and an acquisition layer. The absorbent core comprises a homogeneous blend of fibers comprising a first group of short, low denier, hydrophilic fibers and a second group of longer, higher denier synthetic fibers. The first group of fibers is selected from a group comprising natural fibers, synthetic fibers or cross-linked cellulose fibers. The second group of fibers comprises between about 5 and 90% of said absorbent core, by weight. The absorbent core is compressed to a density of at least about 0.09 $g/cm^3$ (1.5 $g/in.^2$).

The blended core serves as the principal absorbent layer in the absorbent article. The absorbent article does not rely on a separate fluid transfer layer to keep the absorbent core from distorting (as does the Matthews, et al. sanitary napkin). The blended core can be, and preferably is, compressed in the presence of moisture. This creates bonds which provide the absorbent core with increased structural integrity. The blended core contains a sufficient number of moisture insensitive fibers to regain its volume when first wetted in use even if the core material comes in contact with moisture during manufacture. The crimped fibers also entangle each other when the core is compressed. This entanglement of fibers aids the core in retaining its density prior to use.

DETAILED DESCRIPTION OF THE INVENTION

1. Introduction

The present invention relates to absorbent articles such as diapers, sanitary napkins, adult incontinence devices, and the like, which have absorbent cores comprised of blends of different types of fibers.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include diapers, sanitary napkins, pantiliners, and incontinent pads, and the like. The term "disposable" refers to articles which are intended to be discarded after a single use and preferably recycled, composted, or otherwise disposed of in an environmentally compatible manner. (That is, they are not intended to be laundered or otherwise restored or reused as an absorbent article). In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

Figure 1:
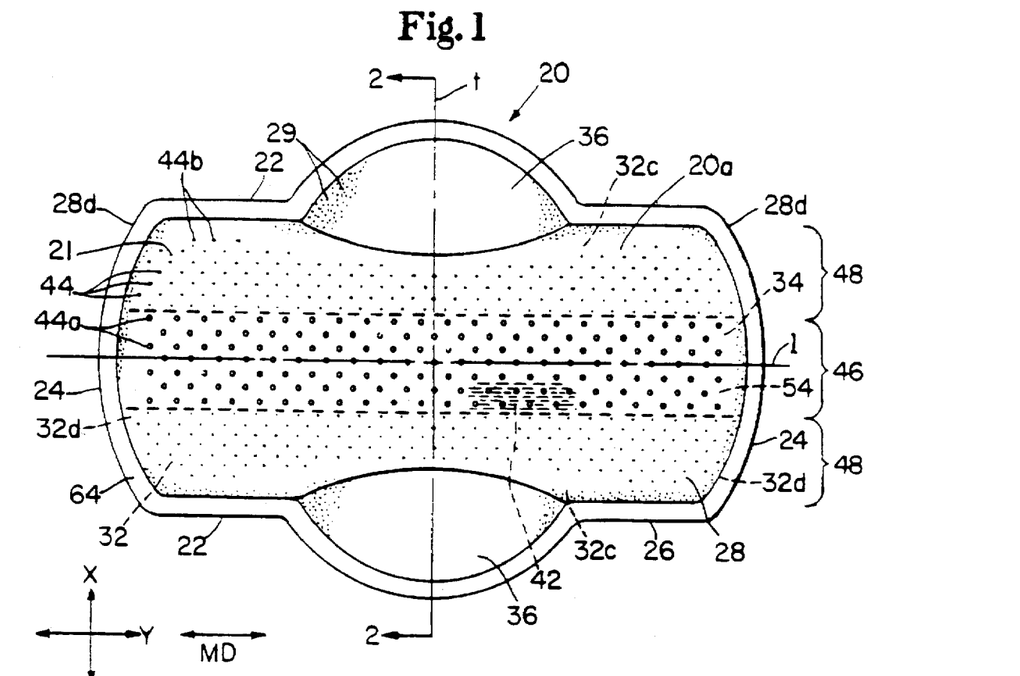
FIG. 1 is a top plan view of a preferred sanitary napkin embodiment of the present invention.

The sanitary napkin 20 has two surfaces, a body-contacting surface or "body surface" 20A and a garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction. FIG. 1 shows that the sanitary napkin 20 also has two spaced apart longitudinal or side edges 22 and two spaced apart transverse or end edges (or "ends") 24, which together form the periphery 26 of the sanitary napkin 20.

The sanitary napkin 20 can be of any thickness, including relatively thick or relatively thin. The embodiment of the sanitary napkin 20 shown in FIGS. 1–3 of the drawings is intended to be an example of a relatively thin sanitary napkin. It should be understood, however, when viewing these figures the number of layers of material shown cause the sanitary napkin 20 to appear much thicker than it actually is. A "thin" sanitary napkin 20 preferably has a caliper of less than about 3 millimeters. The thin sanitary napkin 20 shown should also preferably be relatively flexible, so that it is comfortable for the wearer.

Figure 2:
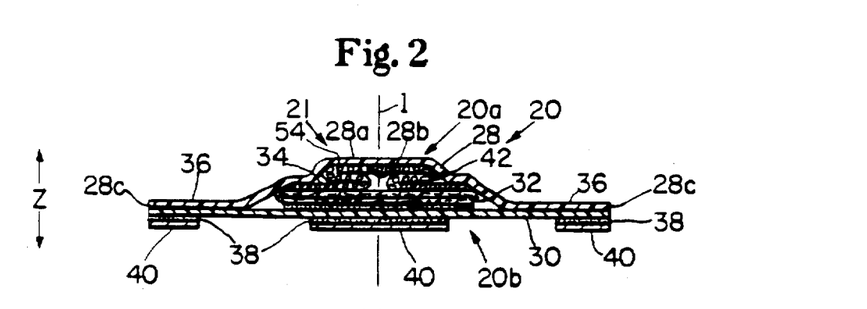
FIG. 2 is a simplified transverse cross-sectional view taken along line 2—2 of FIG. 1.

FIG. 2 shows the individual components of the sanitary napkin. The sanitary napkin 20 of the present invention generally comprises at least three primary components. These include a liquid pervious topsheet 28, a liquid impervious backsheet (or "barrier means") 30, and an absorbent core 32. The absorbent core 32 is positioned between the topsheet 28 and the backsheet 30. The sanitary napkin 20 shown in FIG. 2 preferably also comprises a liquid pervious acquisition layer (or acquisition sheet) 34. The acquisition layer 34 may be a separate element positioned between the topsheet 28 and the absorbent core 32, or it may comprise part of the topsheet 28 or part of the core 32. The sanitary napkin 20 preferably also includes optional side flaps or "wings" 36 that are folded around the crotch portion of the wearer's panties. The sanitary napkin 20 shown also has an adhesive fastening means 38 for attaching the sanitary napkin 20 to the undergarment of the wearer. Removable release liners 40 cover the adhesive fastening means 38 to keep the adhesive from sticking to a surface other than the crotch portion of the undergarment prior to use.

2. Individual Components of the Absorbent Article

The individual components of the sanitary napkin 20 will now be looked at in greater detail.

A. The Topsheet

The topsheet 28 comprises a liquid pervious component that is in close proximity to the skin of the user when the sanitary napkin 20 is in use. The topsheet 28 is preferably as compliant, soft feeling, and non-irritating to the user's skin as possible. The topsheet 28 should further exhibit good strikethrough and a reduced tendency to rewet, permitting the bodily discharges to rapidly penetrate it and flow toward the core 32, but not allowing such discharges to flow back through the topsheet 28 to the skin of the wearer. The topsheet 28 is also preferably opaque to mask menses and other exudates that have penetrated the topsheet 28.

The topsheet 28 has two sides (or faces or surfaces), including a body-facing side 28A and a garment-facing side (or core-facing side) 28B. The body-facing side 28A of the topsheet 28 generally forms at least a portion of the body-contacting surface ("body surface") 20A of the sanitary napkin 20. The topsheet 28 has two longitudinal edges 28C and two end edges 28D. (A similar numbering system will be used for the other components of the sanitary napkin. That is, the side of the component facing the wearer's body will be designated by the number of the component and a reference letter "A". The side facing the wearer's undergarments will be designated by the number of the component and the letter "B". The side and end edges will be designated by the number of the component and the reference letters "C" and "D" respectively.)

A suitable topsheet 28 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven materials for use in the topsheet 28 can be comprised of natural fibers (e.g., wood or cotton fibers), synthetic fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers. Apertured formed films are generally preferred for the topsheet 28 because they are pervious to liquids and, if properly apertured, have a reduced tendency to allow liquids to pass back through and rewet the wearer's skin.

Suitable formed films are described in U.S. Pat. No. 3,929,135 issued to Thompson on Dec. 30, 1975, U.S. Pat. No. 4,324,426 issued to Mullane et al. on Apr. 13, 1982, U.S. Pat. No. 4,342,314 issued to Radel et al. on Aug. 3, 1982, U.S. Pat. No. 4,463,045 issued to Ahr, et al. on Jul. 31, 1984, and U.S. Pat. No. 5,006,394 issued to Baird on Apr. 9, 1991. Additional suitable formed and hydro-formed films are described in U.S. Pat. Nos. 4,609,518, 4,629,643, 4,695,422, 4,772,444, 4,778,644, and 4,839,216 issued to Curro, et al., U.S. Pat. No. 4,637,819 issued to Ouellette, et al. In other embodiments, the topsheet 28 may comprise a nonwoven material overlying a plastic film. Such a topsheet is described in greater detail in U.S. patent application Ser. No. 07/794,745 filed by Aziz, et al. on Nov. 19, 1991. Still other materials suitable for use as a topsheet are described in U.S. Pat. No. 4,775,579 issued to Hagy, et al. on Oct. 4, 1988, U.S. Pat. No. 5,023,124 issued to Kobayashi on Jun. 11, 1991 and in European Patent Application 0 304 617 A2 published Mar. 1, 1989 in the name of Suda, et al.

Figure 7:
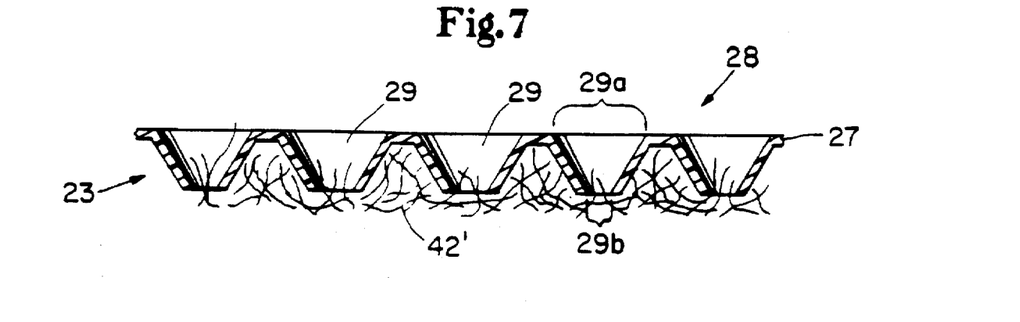
FIG. 7 is a simplified schematic view of a topsheet material which comprises an apertured film with entangled nonwoven fibers.

In another embodiment (shown in FIG. 7), the topsheet 28 may comprise fiber-entangled film. The term "fiber-entangled film" refers to apertured films having fibers entangled in and around their apertures 29. The apertured film of such a topsheet could comprise any of the films or scrims described above. The film has nonwoven fibers 42' mechanically or thermo-mechanically entangled therewith. The fibers are preferably entangled along or from the direction of the core-facing side 28B. The fiber-entangled topsheet 28 material provides more intimate contact between the apertured film 27 and the nonwoven fibers 42'. This can create advantages of improved liquid transport through the film to the fibers 42' and the underlying layers such as the absorbent core 32 or the acquisition layer 34. It may also provide improved comfort since the film 27 will be less likely to separate from the underlying entangled fibers 42', thereby preventing the film 27 from moving into the crevices of the wearer's body.

In still another preferred embodiment (shown in FIG. 8), the sanitary napkin 20 is comprised of components that are extensible (i.e., capable of stretching, particularly in the longitudinal direction) when the sanitary napkin is worn. Preferably, the sanitary napkin 20 is capable of elongating between about 15% and about 40% of its unstretched length. This extensibility provides better in-use fit, sustained attachment to the wearer's undergarments, comfort, and decreased staining. In other embodiments, only limited portions of the components of the sanitary napkin 20 need be capable of stretching.

Figure 8:
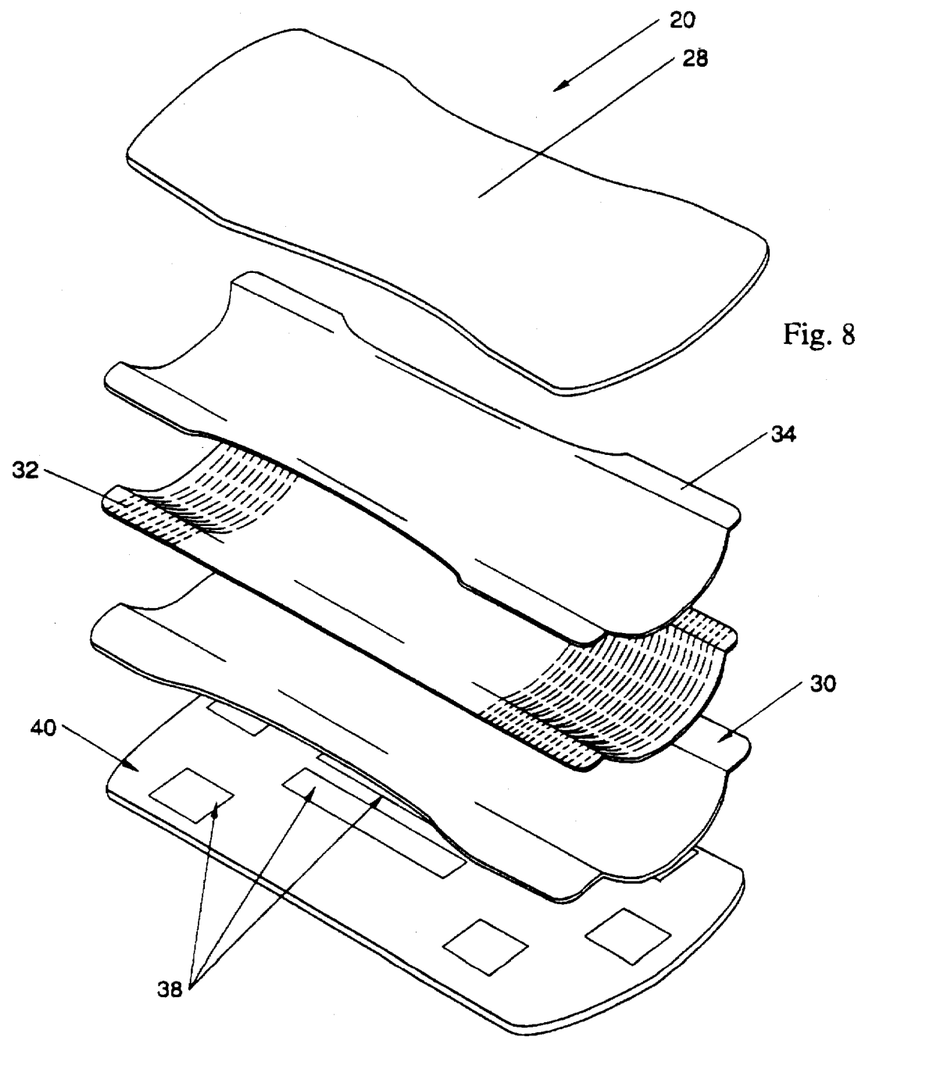
FIG. 8 is an exploded perspective view showing the assembly of a sanitary napkin which contains extensible components.

One type of topsheet 28 for use in the embodiment shown in FIG. 8 can be made in accordance with U.S. Pat. No. 4,463,045 and ring rolled to provide it with a degree of longitudinal extensibility. Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in the following PCT Patent applications, all published on Sep. 17, 1992: Publication Nos. WO 92/25444 published in the name of Gerald M. Weber et al.; WO 92/15446 published in the name of Kenneth B. Buell et al.; and, WO 92/15445 published in the name of Gerald M. Weber et al. on Sep. 17, 1992. The fold lines in the corrugations of the topsheet should run in the transverse direction so the topsheet is longitudinally extensible. Such a topsheet is described in greater detail in the following U.S. patent applications which were filed on Jul. 23, 1991: Ser. No. 07/734,404 filed in the names of Thompson, et al.; U.S. patent application Ser. No. 07/734,392 filed in the names of Thompson, et al.; and, Ser. No. 07/734,405 filed in the names of Buenger, et al. These latter three patent applications may be referred to collectively as the "Capillary Channel Fiber" patent applications.

In addition, in preferred embodiments of the present invention, at least a portion of the topsheet 28 is treated with a surfactant. This can be accomplished by any of the common techniques well known to those skilled in the art. Suitable methods for treating the topsheet with a surfactant are described in a number of references, including U.S. Pat. Nos. 4,950,264 and 5,009,653 issued to Osborn, and in U.S. patent application Ser. No. 07/794,745 filed by Aziz, et al. on Nov. 19, 1991. The latter patent application teaches treating the apertured film component of a nonwoven/apertured thermoplastic formed film topsheet with a surfactant. The surfactant is preferably incorporated into the resin used to make the thermoplastic formed film.

Treating the topsheet 28 with a surfactant renders the surface of the topsheet 28 more hydrophilic. This results in liquid penetrating the topsheet 28 faster than it would if the topsheet were not treated. This diminishes the likelihood that body fluids will flow off topsheet 28 rather than being drained through the topsheet 28.

B. The Acquisition Layer

The acquisition layer (or "acquisition/distribution layer", or acquisition sheet") 34 is shown in FIG. 2. It is positioned between the topsheet 28 and (at least a portion of) the absorbent core 32.

In the embodiment shown in FIG. 2, the acquisition layer 34 is a folded sheet of nonwoven material. It should be understood, however, that the acquisition layer 34 need not be a folded sheet. The terms "layer" or "web", as used herein, include, but are not limited to single unfolded sheets, folded sheets, strips of material, loose or bonded fibers, multiple layers or laminates of material, or other combinations of such materials. These two terms are thus, not limited to single unfolded layers or sheets of material.

In FIG. 2, the acquisition layer 34 is a "double" z-folded sheet. The sheet 34, is more specifically folded so that when the sanitary napkin is cut along the transverse line, the left half of the folded sheet appears as a reverse "z" in cross section and the right half appears as a "z". The sheet 34 is preferably folded so that it has an upper portion 54 that appears as a rectangular strip in plan view. Such a folded arrangement is described in greater detail in U.S. patent application Ser. No. 07/605,583 filed on Oct. 29, 1990 in the name of Visscher, et al.

Figure 3:
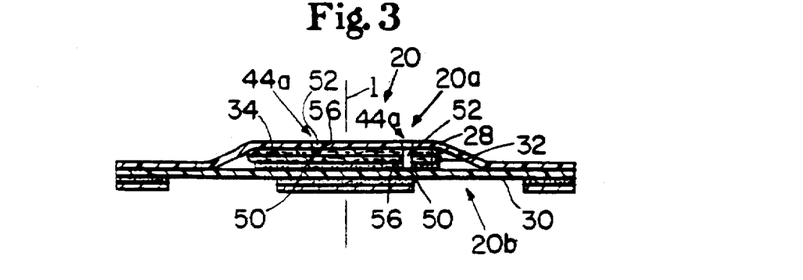
FIG. 3 is a simplified transverse cross-sectional view similar to that of FIG. 2, showing an alternative arrangement of the components of the sanitary napkin.

FIG. 3 is a simplified cross-sectional view similar to that of FIG. 2, showing an alternative arrangement of the components of the sanitary napkin 20. In FIG. 3, rather than being a separate layer that is located on top of the core 32, the acquisition layer 34 is an integral layer (or component) that comprises the top layer of a laminated absorbent core 32 structure.

The acquisition layer 34 serves to improve wicking of exudates over and into the absorbent core 32. The combination of the acquisition layer 34 and the topsheet 28 also provides the sanitary napkin with the enhanced gush acquisition and enhanced wipe acquisition described in greater detail in U.S. Pat. Nos. 4,950,264 and 5,009,653 issued to Osborn. (Thus, the acquisition layer 34 may be referred to as a "wipe acquisition sheet").

The acquisition layer 34 should have several characteristics. The acquisition layer 34 should be liquid permeable. The acquisition layer 34 is also preferably compliant, soft feeling, and non-irritating to the user's skin. It can be made from any materials that are capable of dispersing exudates as described in the patents listed above issued to Osborn. The materials are preferably also capable of having the topsheet 28 fused to them. The acquisition layer 34 may also be provided with stretch properties. The acquisition layer 34 has a body-facing face (or side) 34A, and a garment-facing face 34B.

The acquisition layer 34 should be hydrophilic. The fibers or yarns 42 comprising the acquisition layer 34 may be inherently hydrophilic. Alternatively, they may be treated to render them hydrophilic. Suitable methods for rendering fibers hydrophilic include treating them with a surfactant. The fibers can be treated by spraying the material comprising the acquisition layer with a surfactant or immersing the material into the surfactant. A more detailed discussion of such a treatment and hydrophilicity is contained in U.S. Pat. Nos. 4,988,344 and 4,988,345 issued to Reising, et al. and to Reising, respectively. The hydrophilicity of these fibers allows the acquisition layer 34 to draw liquid exudates through the topsheet 28 from below.

The acquisition layer 34 may be comprised of woven or nonwoven materials. These materials may be synthetic, or partially synthetic and partially natural materials. Suitable synthetic fibers include polyester, polypropylene, polyethylene, nylon, viscous rayon fibers, or cellulose acetate, with polyester fibers being preferred. Suitable natural fibers include cotton, cellulose, or other natural fibers. The acquisition layer 34 may also be at least partially comprised of cross-linked cellulose fibers. Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,898,642, issued Feb. 6, 1990 to Moore, et al.; and U.S. Pat. No. 4,935,022 issued Jun. 19, 1990 to Lash et al. The acquisition layer 34 may also be comprised of capillary channel fibers (that is, fibers having channels formed therein, preferably, on their exterior surfaces). Such fibers are described in greater detail in EPO Patent Application 0 391,814 published Oct. 10, 1990, and in the Capillary Channel Fiber patent applications. The acquisition layer 34 can also be comprised of combinations of the above materials, such as blends of fibers similar to those described below for use in the absorbent core, or any equivalent material or combinations of materials.

The fibers 42 of the acquisition layer 34 are preferably oriented primarily in a single direction. Typically, the acquisition layer 34 can be manufactured with its fibers oriented in the machine direction (MD). The acquisition layer 34 can be placed in the product with most of the fibers 42 oriented in the longitudinal direction. (That is, the fibers 42 are generally parallel to the longitudinal centerline L of the sanitary napkin 20). The phrase "generally parallel" to the longitudinal centerline (and similar phrases) as used herein, is intended to include fibers that angle away from the longitudinal centerline. These fibers are considered to be generally parallel as long as they are oriented more in the longitudinal direction than the transverse direction. The orientation of the fibers 42 of the acquisition layer 34 causes liquid exudates deposited on the acquisition layer 34 to preferentially wick and be distributed toward the ends 32D of the absorbent core 32.

The acquisition layer 34 may be any suitable size. The acquisition layer 34 need not extend the full width of the absorbent core 32. The acquisition layer 34 can, for instance, be in the form of a strip positioned similarly to (and of a size similar to) the upper portion 54 of the z-folded sheet shown in FIGS. 1 and 2.

The acquisition layer 34, if nonwoven, can be made by a number of different processes. These include, but are not limited to the following: meltblown, spunbonded, carded, the latter including, in order of preference, thermally-bonded, through-air bonded, powder bonded, latex bonded, solvent bonded, or spunlaced. The latter processes may be preferred because it is easier to orient the fibers in a single direction in such processes.

In one preferred embodiment, the acquisition layer 34 comprises a spunlace nonwoven web comprised of permanently wettable fibers. Preferably, the acquisition layer 34 is a 30 g/yard$^2$ (35 g/m$^2$) polyethylene theraphtalate (or PET) spunlace nonwoven web. Spunlaced fabrics of this type are manufactured by the Veratec Company of Walpole, Mass.

The spunlace nonwoven web is formed in such a way that most of the fibers are oriented in a single direction.

The fibers of this preferred acquisition layer 34 material are made of a PET resin and are coated with a proprietary permanently wettable finish known as CELWET. These fibers are available from the Hoechst Celanese Corporation of Charlotte, N.C. The CELWET finish is particularly preferred for use in sanitary napkins having a topsheet 28 comprising an apertured film or scrim with hydro-entangled nonwoven fibers because fibers coated with it remain extremely hydrophilic after hydro-entangling processes, and therefore, wick blood very well.

The topsheet 28 is secured in contact with the acquisition layer 34. This relationship results in liquid penetrating topsheet 28 faster. In conventional products, the topsheet 28 is initially maintained in contact with the underlying layer by applying adhesive between the underlying layer and the topsheet 28.

In the embodiments of the present invention shown in FIGS. 1–3 of the drawings, the topsheet 28 is joined in a face-to-face relationship with the underlying acquisition layer 34 by fusion bonding the topsheet 28 and the acquisition layer 34. The faces of the topsheet 28 and the acquisition layer 34 are fused on those portions of the respective faces that are on the main body portion 21 of the sanitary napkin which are inboard of any liquid impervious seam, such as the seam 64 around the periphery 26 of the sanitary napkin 20. (The term "inboard" means toward the intersection of the longitudinal and transverse centerlines).

The fusion of the topsheet 28 and the acquisition layer 34 can be accomplished by heat and/or pressure bonds, ultrasonic bonds, dynamic mechanical bonds, and the like. Pressure can be applied in any suitable manner, such as by moving the two components between counter-rotating rolls, placing the materials on an anvil and forcing a platen down on the materials, applying vacuum pressure, and the like.

Suitable means that can be adapted for use in fusing the topsheet 28 to the acquisition layer 34 are described in at least some of the following patents: U.S. Pat. No. 4,430,148 Schaefer, U.S. Pat. No. 4,515,595 Kievit, et al., U.S. Pat. No. 4,531,999 Persson, et al., U.S. Pat. Nos. 4,710,189 and 4,808,252 issued to Lash, U.S. Pat. No. 4,823,783 Willhite, Jr., et al. and U.S. Pat. Nos. 4,854,984 and 4,919,756 issued to Ball, et al.

The fusion bonding preferably comprises a pattern of individual fusion bonds 44. The individual bonds 44 can be of any plan view shape. For instance, the bonds 44 can be in the form of straight or curved lines, geometric shapes such as circles, squares, rectangles, diamonds, and the like, or irregular shapes. The bonds 44 can be arranged in many different manners.

FIG. 1 shows one preferred bonding pattern. The fusion bonds 44 comprise discrete points of attachment which comprise circular bonds. The bonds 44 are arranged in a pattern that is preferably distributed over the entire body surface 20A of the main body portion 21 of the sanitary napkin. (The main body portion 21 is the part of the sanitary napkin from which the flaps extend). The bonding pattern shown in FIG. 1 comprises a plurality of larger bonds 44A and a plurality of small bonds 44B. The large bonds 44A are positioned in the longitudinal central region 46 of the sanitary napkin. The smaller bonds 44B are positioned in the longitudinal side regions 48 of the sanitary napkin.

The topsheet 28 and acquisition layer 34 (or other underlying layer) may also be secured at least partially by any other suitable attachment means or combinations of such other means and the above attachment means. The topsheet 28 and the acquisition layer 34 can also be at least partially attached by any means known in the art, such as by adhesives.

If adhesives are used, the adhesives can be applied in a uniform continuous layer, a patterned layer, or an array of separate lines, spirals, or spots of adhesive. The adhesive attachment preferably comprises an open pattern network of filaments of adhesive as is disclosed in U.S. Pat. No. 4,573,986 issued to Minetola, et al. on Mar. 4, 1986, or an open pattern network of filaments comprising several lines of adhesive filaments swirled into a spiral pattern as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Suitable adhesives are manufactured by the Findley Adhesives Incorporated of Elm Grove, Wis. and marketed as H-1077 or H-1137.

In still other embodiments, the topsheet 28 and acquisition layer 34 may be at least partially attached by mechanical and thermo-mechanical entanglement.

C. The Absorbent Core

The absorbent core 32 is positioned between the topsheet 28 and the backsheet 30. The absorbent core 32 provides the means for absorbing menstrual fluid and other body exudates. The absorbent core 32 is generally at least slightly compressible (but preferably not collapsible), conformable, and non-irritating to the user's skin.

The absorbent core 32 used in the present invention is referred to as a "blended" core. This particular core arrangement is shown in FIGS. 1–3 as a thin web for use in thin products, and in FIGS. 4–6 in a relatively thick sanitary napkin 20.

The blended absorbent core 32 comprises a batt of fibers, preferably in the form of a homogeneous blend of fibers. The blended core 32 is comprised of at least two groups (or types) of fibers. These include a first group (or type) of low denier, relatively short, hydrophilic fibers. The second group (or type) of fibers comprises from about 5%, preferably at least about 10 or 20% to about 90% of higher denier, longer moisture insensitive synthetic fibers. The blend ratio of the two groups of fibers can be varied to produce the properties desired for different types of absorbent articles. (All percentages specified in this description are by weight unless stated otherwise).

The first group of fibers can comprise natural fibers such as cotton, or (cellulose which may be in the form of comminuted wood pulp fibers known as airfelt). The first group of fibers can alternatively or additionally comprise synthetic fibers, including but not limited to, PET, polypropylene, polyethylene, rayon, chemical thermal mechanical pulp (or "CTMP" or TMP"), ground wood, or chemically modified fibers, such as cross-linked cellulose fibers. The fibers in the first group of fibers are either inherently hydrophilic, or they may be rendered hydrophilic by treating them in any of the manners described previously to render them hydrophilic.

Performance is improved by selecting a relatively stiff fiber which maintains a substantial portion of its compression resistance when wetted for the fibers in the first group. (That is, the fibers should have a high compressive modulus.) Preferably, the fibers selected are both compression resistant under wet and dry conditions, and are wet and dry resilient (i.e., they tend to both resist compression and to spring back when compressed). Cross-linked cellulose fibers are especially preferred for these criteria. (It is understood, however, that cross-linked cellulose fibers are sufficiently modified that they may no longer be considered as either cellulosic, or as natural fibers, per se.)

The second group of fibers should also be of high compressive modulus and should maintain a relatively high modulus when wetted. The second group of fibers should also preferably be wet and dry resilient. Suitable fibers include, but are not limited to synthetic fibers comprised of any of those materials specified above as being suitable for use as the fibers of the acquisition layer 34. (Fiber lengths, denier, etc. are, however, not necessarily the same. Some preferred fiber lengths, etc. are described below).

The fibers in the second group of fibers are preferably longer than the fibers in the first group of fibers. Preferably, the fibers in the second group of fibers are greater than or equal to about ¼ inch (about 0.6 cm.) long, and are more preferably greater than or equal to about ½ inch (about 1.3 cm.) long. The denier of the fibers in the second group of fibers is preferably greater than the denier of the fibers in the first group of fibers. The fibers in the second group of fibers preferably have a denier per filament of between about 4 or 4.5 and about 50 or 60, or more preferably between about 6 and about 40. More preferably still, the denier is between about 12 or 15 and about 30, and most preferably between about 12 and about 25.

The fibers in the second group of fibers are moisture insensitive. That is, the fibers in this group are not subtantially affected by the presence of moisture (and, thus, will not collapse when wetted). These fibers may transport liquids along their surfaces, however. The fibers in the second group may be hydrophilic, hydrophobic, or partially hydrophilic and partially hydrophobic. The fibers in the second group of fibers preferably have at least some hydrophilic component (which may be a cellulosic component). The fibers in the second group of fibers can be provided with a hydrophilic component in a number of suitable ways. These include, but are not limited to coating or treating the fibers to render them, or at least their surfaces, hydrophilic.

One suitable type of synthetic fibers for use in the second group of fibers are crimped polyester fibers. Other suitable synthetic fibers are available from Eastman Kodak Textile Fibers Division Kingsport, Tenn. as the KODEL 200 and 400 Series PET fibers. One suitable type of synthetic binder fiber is the KODEL 410 fiber. A suitable polyester fiber is the KODEL 431 fiber. These KODEL fibers are preferably crimped at a crimping frequency of between about 5 and 7, preferably about 6, more preferably 6.3 crimps per linear inch (i.e., per 2.5 cm.). The fibers are preferably crimped at a crimping angle of between about 70° to about 91°, preferably about 88°. Crimping provides the fibers with improved resilience, among other desired properties. The fibers have a denier of 15 per filament and a length of about 0.5 inch (about 1.3 cm.). They may be coated with a hydrophilic or hydrophobic finish by any suitable method known in the art.

In an alternative embodiment, it is possible to replace the natural fibers in the first group of fibers with very short, low denier, synthetic fibers (with hydrophilic surfaces). The blended core 32 in this situation would consist of short, low denier, hydrophilic first group of synthetic fibers (such as polyester fibers with a CELWET finish) and long, high denier second group of synthetic fibers.

Such a blended core may, and preferably does, also contain particles of hydrogel-forming polymer gelling agents to increase the absorptive capacity of the core.

The polymeric gelling agent which is employed in the absorbent core 32 will generally comprise particles of a hydrogel-forming polymer material. The term "particles", as used herein, can refer to particles in any form, such as in the form of pellets, flakes, or fibers. The characteristics of preferred types of polymer materials used therein, and types of methods which can be used for preparing these polymer particles) are described in greater detail in U.S. Pat. No. 4,673,402 issued to Weisman, et al, U.S. Pat. No. 5,009,653 issued to Osborn and the patents incorporated by reference in those patents, the disclosures of which are all incorporated by reference herein.

In one preferred embodiment, the hydrogel-forming polymer gelling agents comprise "high-speed" absorbent gelling materials. The term "high-speed" absorbent gelling materials, as used herein, means those absorbent gelling materials that are capable of absorbing exudates at such a rate that they reach at least about 40%, preferably at least about 50%, and most preferably at least about 90% of their capacity in less than or equal to about 10 seconds. A suitable method for the percent rate of capacity is described in U.S. patent application Ser. No. 07/637,090 filed by Noel, et al. on Jan. 3, 1991, and in PCT International Publication No. WO 92/11831 published in the name of Feist, et al on Jul. 23, 1992. In alternative embodiments, it is also possible for the high-speed absorbent gelling materials to be mixed with other types (or ordinary speed) absorbent gelling materials.

Preferably, in the embodiment described immediately above, the high-speed absorbent gelling materials are in fibrous form. Such fibers (though not necessarily high-speed fibrous absorbent gelling materials) are discussed more fully in U.S. Pat. No. 4,855,179, issued Aug. 8, 1989, to Bourland, et al. The term "fibrous absorbent gelling materials", as used herein, is intended to include absorbent gelling materials in the form of fibers that are comprised entirely of absorbent gelling material and bi-component fibers that are comprised at least partially of other materials which have their surfaces coated with absorbent gelling materials. Suitable fibrous absorbent gelling materials include an acrylic fibrous material available under the tradename Lanseal F from the Choli Company, LTD., of Higashi, Osaka, Japan, and a carboxymethylcellulose fibrous material available under the tradename Aqualon C from Hercules, Inc. Suitable high speed fibrous absorbent gelling materials are known as FIBER-SORB SA7000 or SA7200 formerly manufactured by Arco Chemical Company of Newton Square, Pa.

The effective utilization of hydrogel-forming polymer gelling agents is believed to be improved in such a blended core. The use of higher concentrations of hydrogel-forming polymer gelling agents may also be possible.

The blended absorbent core 32 is preferably compressed to a density of at least about 1.5 g/cubic inch (about 0.09 g/cm$^3$). The blended core 32 may be compressed to densities at least as high as about 4.0 g/cubic inch (about 0.25 g/cm$^3$) to improve fluid wicking while still maintaining good softness and flexibility. (The density values specified above do not include the weight of any particles of absorbent gelling material).

The blended core 32 may be compressed to densities as high as about 0.35 g/cm$^3$ to about 0.40 g/cm$^3$. These higher density cores may become rather stiff, however. Therefore, if the core is compressed to densities of about 0.35 g/cm$^3$ to about 0.40 g/cm$^3$, it is preferably mechanically flexed or otherwise manipulated to make it more flexible before it is placed in use.

Densification may be applied to the entire absorbent core 32 or only to selected portions. Patterned densification allows tailoring of the fluid handling properties to a specific need. For example, the density may be very low in the fluid target area to maximize fluid acquisition speed, and density may be very high near the core edges to maximize fluid wicking.

In one particularly preferred embodiment, the improved absorbent core 32 is an air-laid blend comprised of approximately 15% of 0.5 inch long, 15 denier per filament crimped polyester fibers and approximately 85% of cross-linked cellulose fibers. The polyester fibers are preferably crimped at a crimping frequency of about 6 crimps per linear inch (i.e., per 2.5 cm.). The fibers are preferably crimped at a crimping angle of about 90°. The core 32 is preferably compressed to a density of about 1 g/cubic inch (about 0.06 g/cm$^3$).

The absorbent core 32 may optionally be sprayed with latex to give the core added integrity. Latex may be applied by spraying it on one or both faces of the core. One latex suitable for this purpose is known as TR 520 available from Rhom & Haas of Philadelphia, Pa. The latex may be heated until it cross-links or cures.

The absorbent core 32 may also be treated with a surfactant to increase the ability of the core to receive liquids (i.e., to transport liquids into and through the core). This is useful particularly when the core contains a high concentration of synthetic (e.g. polyester) fibers. Suitable surfactants include those known commercially as Brij 76, PEGOSPERSE 200ML, and PLURONIC L92. The surfactant can be applied in any suitable manner. Preferably, the surfactant is applied by spraying it on the body-facing side 32A of the absorbent core.

Figure 9:
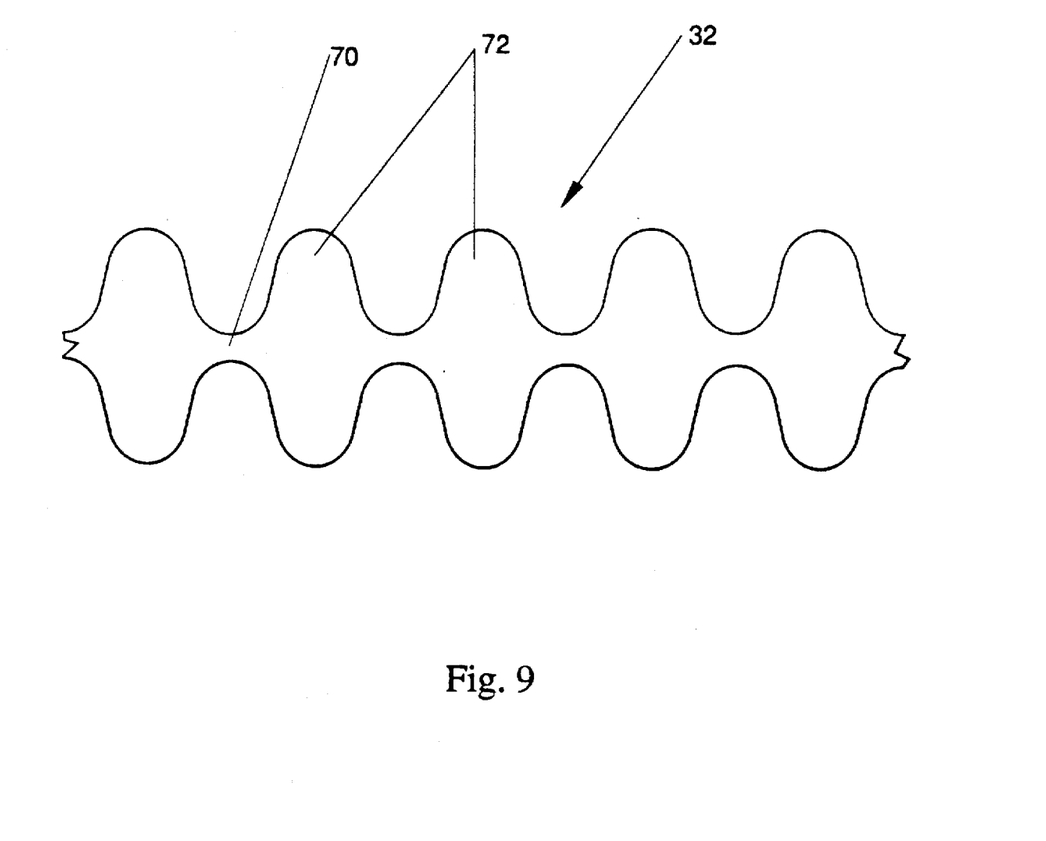
FIG. 9 is a schematic cross sectional view of a portion of a blended absorbent core that is provided with a plurality of ribs.

FIG. 9 shows that the core 32 may also optionally be provided with a plurality of spaced compressed areas 70 that have ribs 72 therebetween. The ribs 72 are preferably generally oriented in the longitudinal direction. The compressed areas 70 promote wicking of fluids along their length. The compressed areas 70 can be formed by any process suitable for compressing a web. The core 32, thus, has a density differential between the compressed areas 70 and the ribs 72. The core 32 shown in FIG. 9 should have at least one region (i.e., either the compressed areas 70 or the ribs 72) that is compressed to the densities specified herein. Preferably, both regions are within the density ranges specified herein.

The blended absorbent core 32 can be used as the entire core or it can be used as one or more layers in a layered construction. The blended absorbent core 32 can be used with or without the acquisition layer 34.

Figure 4:
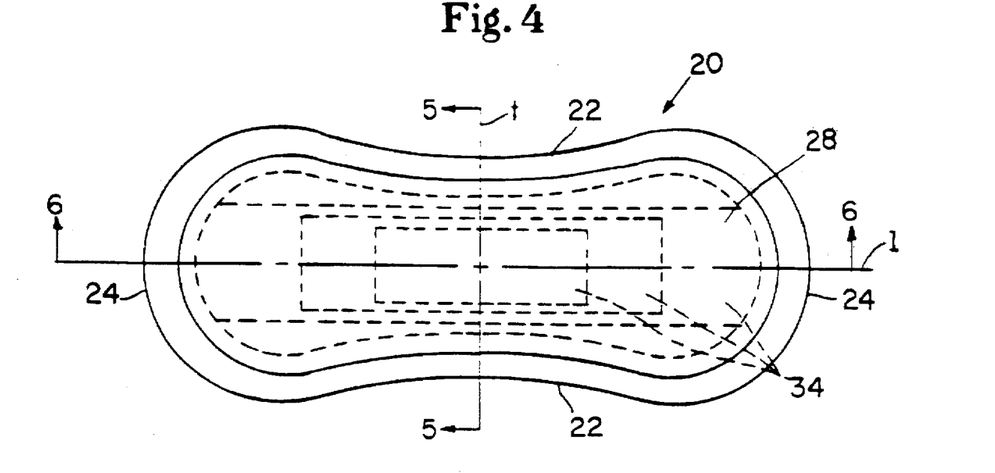
FIGS. 4–6 are top plan and simplified cross-sectional views along lines 5—5 and 6—6, respectively, of a thick sanitary napkin with a profiled shape.
Figure 5:
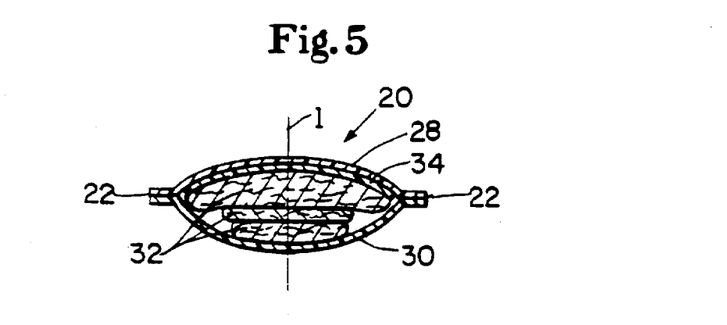
Figure 6:
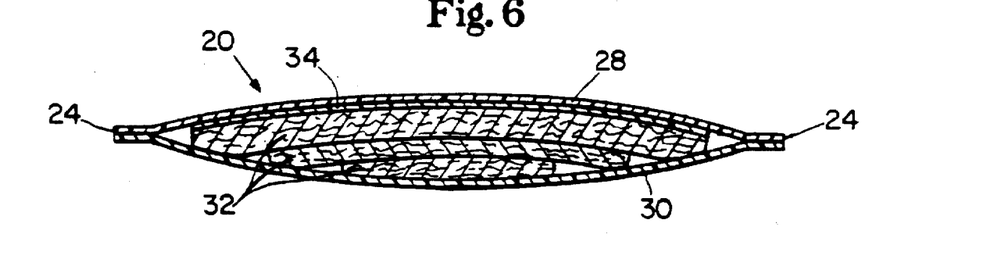

FIGS. 4–6 show an example of a core 32 in which layers of core material are used to produce a "profiled" sanitary napkin 20. The profiled sanitary napkin 20 is thicker in the center of the sanitary napkin and tapers so it becomes thinner toward the edges 22 and 24. FIGS. 5 and 6 show that such a profiled sanitary napkin 20 can be made by stacking layers having relatively large length and width dimensions on top of those with smaller length and widths (or vice versa).

In a layered construction, one or more layers can consist of all cellulose or cellulose/hydrogel-forming polymer material blends. The layers could also have differing fiber and/or absorbent gelling material content. For example, a higher percentage of absorbent gelling material could be provided in the lower layers to provide additional liquid storage capacity.

The blended absorbent core 32 is believed to provide enhanced performance. The blended absorbent core is believed to provide improved fluid acquisition speed and absorptive capacity. These improvements are believed to result in reduced leakage. The absorbent core can also be made smaller and thinner to make the article more comfortable and discrete to wear. The strength of the core is also believed to be improved because of the longer crimped synthetic fiber content. These improved characteristics are believed to be due to a number of factors.

Absorbent cores of the subject composition have a lower wet density than cores composed entirely of cellulose. The lower wet density results from the presence of the synthetic fibers. Water is not absorbed into the synthetic fibers, therefore, the modulus of the fibers does not change when wetted and they do not collapse. Wetting of the cellulose fibers causes the fiber-to-fiber hydrogen bonds in these fibers to release. The lower wet density provides the blended absorbent core with improved fluid acquisition speed and higher absorptive capacity. The lower wet density allows any hydrogel-forming polymer materials included in the fiber matrix to absorb a higher quantity of liquids since there is more room for the polymer materials to swell.

The first group of fibers is believed to aid in reducing leakage. The blended core provides a quantity of small capillaries which a core comprised of 100% of the type of fibers described as being suitable for use as the second group of fibers would not have. These smaller capillaries allow the core to pull liquids through the topsheet and away from the wearer's skin. This improves leakage performance due to a reduction in the volume of fluid which can exit the product by running along the surface of the topsheet and the surface of the wearer's skin.

The first group of fibers of the blended core also provides a wicking capability. This capability results from the small capillaries mentioned above. This capillarity can be enhanced by densification of the core. The cellulose allows the core to be maintained at a high density when dry that is generally not achievable with pure synthetics. The presence of the synthetic fibers allows the portions of the core that are wetted to expand. This reduces the density of these wetted portions. The neighboring densified areas which are still dry have a high density. This provides these neighboring dry areas with small capillaries. The liquids will, as a result, tend to wick into these neighboring areas. This maintains absorptive capacity and acquisition speed, and also dries the surface of the sanitary napkin.

The crimped synthetic fibers are believed to provide the core with improved compression resistance and resiliency. The resiliency maintains the void space in the core even after liquids are absorbed into the core and pressure is applied to the core. The void space provides additional storage space for absorbed liquids. It also provides additional space in which the absorbent gelling materials can swell after taking in liquids.

The absorbent core 32 can additionally comprise any other types of materials used in the art in absorbent articles. Examples of suitable additional core materials include creped cellulose wadding, peat moss, etc., or any equivalent material or combinations of materials.

The characteristics of other types of absorbent cores are described in greater detail in the patents and documents incorporated by reference herein. Additional characteristics are described in the patents and other documents incorporated by reference in those documents. The disclosures of all of these references are incorporated herein. In addition, other suitable absorbent core arrangements are described in U.S. Pat. Nos. 4,988,344 and 4,988,345, and European Patent Application Publication No. 0 198 683, published Oct. 22, 1986 in the name of Duenk, et al. Other possible core 32 materials are described in U.S. Pat. No. 4,475,911 issued to Gellert on Oct. 9, 1984.

The sanitary napkin (or other absorbent article) 20 could also include any additional layers or other components such as are described in the patents incorporated by reference. For example, the absorbent article may comprise an acquisition layer or patch of cross-linked cellulose fibers positioned between the topsheet 28 and the absorbent core 32.

D. The Backsheet

The backsheet 30 is impervious to liquids. The backsheet 30 serves to prevent menstrual fluid and other body exudates from soiling the clothing of the user. Any material used in the art for such purpose can be utilized herein. Suitable materials include embossed or nonembossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 28 overlays only the main body portion 21 and does not extend out to form the top surface of the flaps 36 such as is described in U.S. Pat. No. 5,007,906), the backsheet 30 may be comprised of two layers. In such a case, the backsheet 30 may comprise a first layer of lofted material that forms the core-facing side 30A of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 30B of the backsheet 30, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 30 may also be made of a soft, cloth-like material which is hydrophobic relative to the topsheet 28. A polyester or polyolefinic fiber backsheet 30 has been found to work well. A particularly preferred soft, cloth-like backsheet 30 material is a laminate of a polyester nonwoven material and a film such as described in U.S. Pat. No. 4,476,180 issued to Wnuk on Oct. 9, 1984.

In other embodiments, the backsheet 30 is extensible. A particularly preferred extensible backsheet 30 is an extended adhesive film Formula #198-338 manufactured by the Findley Adhesives Company of Wauwatosa, Wis. which is described in greater detail in the Capillary Channel Fiber patent applications.

As shown in FIGS. 1 and 2, the topsheet 28 is preferably secured to the backsheet 30 along a seam 64 around the periphery 26 of the sanitary napkin 20. The seam 64 can be formed by any means commonly used in the art for this purpose such as by gluing, crimping, or fusing. This is a preferred embodiment for ease of construction. (Other means of uniting the various elements can be used). For instance, other possible embodiments include one in which the absorbent core 32 is essentially completely wrapped with topsheet 28 before it is placed on the backsheet 30. The sanitary napkin 20 can also comprise an absorbent core which possesses sufficient integrity to stand alone and is liquid pervious on one surface while the other surface has been treated to render it liquid impervious.

FIGS. 1 and 2 also show the fasteners, such as adhesive fastening means 38, which are adapted to secure the sanitary napkin 20 to the crotch region of an undergarment. Suitable adhesive fasteners are described in greater detail in U.S. Pat. No. 4,917,697. The fasteners used with the present invention are not limited to adhesive attachment means. Any type of fastener used in the art can be used for such purpose. For example, the sanitary napkin 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990.

The adhesive fastening means 38 are covered by removable release liners, designated 40. The pressure-sensitive adhesives should be covered with release liners 40 to keep the adhesives from sticking to extraneous surfaces prior to use. Suitable release liners are described in U.S. Pat. No. 4,917,697. A suitable wrapper that both serves as a package for a sanitary napkin and as a cover for adhesives on the sanitary napkin is described in U.S. Pat. No. 4,556,146 issued to Swanson, et al. on Dec. 3, 1985.

3. Alternative Embodiments

While several preferred sanitary napkin embodiments of the present invention have been described, numerous other types of sanitary napkins are available and are disclosed in the literature. These could be provided with the fused layers of the present invention. These sanitary napkins include those disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264 and 5,009,653 issued to Osborn on Aug. 21, 1990 and Apr. 23, 1991, respectively; in PCT International Publication No. WO 92/07535 published in the name of Visscher, et al. on May 14, 1992; and in U.S. patent application Ser. No. 07/915,133 filed Jul. 23, 1992 by Osborn, et al.

The terms "pantiliner" or "panty liner" refer to absorbent articles that are less bulky than sanitary napkins which are generally worn by women between their menstrual periods. Suitable absorbent articles in the form of pantiliners that could be provided with the blended absorbent core described herein are disclosed in U.S. Pat. No. 4,738,676 entitled "Pantiliner" issued to Osborn on Apr. 19, 1988.

The term "incontinent article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the blended absorbent core described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991, and in PCT International Publication No. WO 92/11831 published in the name of Feist, et al on Jul. 23, 1992.

The term "diaper" refers to a garment generally worn by infants and incontinent persons which is drawn up between the legs and fastened about the waist of the wearer. Suitable absorbent articles at least some of which are in the form of diapers which could be provided with a blended absorbent core are disclosed in U.S. Pat. No. Re. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986; U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany, et al. on May 30, 1989; U.S. Pat. No. 4,888,231 issued to Angstadt on Dec. 19, 1989; and U.S. Pat. No. 4,909,803 issued to Aziz, et al. on Mar. 20, 1990.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. An absorbent core for an absorbent article, said absorbent core comprising a homogeneous blend of fibers comprising a first group of short, low denier, hydrophilic fibers selected from a group comprising natural fibers, hydrophilic synthetic fibers or cross-linked cellulose fibers, and a second group of longer, higher denier moisture insensitive crimped synthetic fibers, said second group of fibers comprising at least about 5% of said absorbent core, by weight, said absorbent core being compressed in a substantially dry condition to a density of at least about 0.09 g/cm$^3$.

2. The absorbent core of claim 1 wherein when liquids are deposited on said absorbent core, portions of said absorbent core that receive such liquids will become wetted while the portions that surround the wetted portions will initially be unwetted, and said wetted portions will expand when wetted reducing the density of the wetted portions relative to the surrounding unwetted portions so that said unwetted portions have a higher density than said wetted portions and said absorbent core will distribute liquids to said adjacent unwetted portions.

3. An absorbent article comprising:
   a liquid pervious topsheet;
   a liquid impervious backsheet joined to said top sheet; and
   an absorbent core positioned between said topsheet and said backsheet, said absorbent core comprising a plurality of absorbent hydrogel-forming material particles in a homogeneous blend of fibers comprising
      a first group of fibers selected from a group of hydrophilic fibers comprising natural fibers, hydrophilic synthetic fibers or cross-linked cellulose fibers, said fibers in said first group of fibers being less than about 0.6 cm long, having a denier per filament of less than about 6, and being compression resistant, wet and dry resilient; and
      a second group of moisture insensitive polyester fibers, said second group of fibers comprising about 15% of said absorbent core by weight, exclusive of said hydrogel-forming material particles, said fibers in said second group of fibers being greater than or equal to about 1.3 cm long, having a denier per filament of between about 15–25, being crimped at a crimping frequency of between about 5 and 7 crimps per linear 2.5 cm at a crimping angle of between about 70° and 90°, and being compression resistant, and wet and dry resilient, said absorbent core being compressed in a substantially dry condition to a density of between about 0.09 g/cm$^3$ and about 0.25 g/cm$^3$ and said core expanding when wetted.

4. An absorbent article comprising:
   a liquid pervious topsheet;
   a liquid impervious backsheet joined to said topsheet; and
   an absorbent core positioned between said topsheet and said backsheet, said absorbent core comprising a homogeneous blend of fibers comprising a first group of fibers of a first length and first denier and being selected from a group of hydrophilic fibers comprising natural fibers, hydrophilic synthetic fibers or cross-linked cellulose fibers, and a second group of longer, higher denier moisture insensitive crimped synthetic fibers, said second group of fibers comprising at least about 5% of said absorbent core, by weight, said absorbent core being compressed in a substantially dry condition to a density of at least about 0.09 g/cm$^3$ and said core expanding when wetted.

5. The absorbent article of claim 4 wherein the fibers in the first group of fibers are selected from the group consisting of at least one of the following types of fibers: cotton fibers, cellulose fibers, airfelt, rayon, chemical thermal mechanical pulp, ground wood, and cross-linked cellulose fibers.

6. The absorbent article of claim 4 wherein the fibers in the first group of fibers are compression resistant.

7. The absorbent article of claims 4 or 6 wherein the fibers in the first group of fibers are wet and dry resilient.

8. The absorbent article of claim 4 wherein the fibers in the first group of fibers are less than 0.6 cm long.

9. The absorbent article of claim 4 wherein the fibers in the first group of fibers are synthetic and have a denier per filament of less than about 6.

10. The absorbent article of claim 4 wherein the fibers in the second group of fibers are selected from the group consisting of at least one of the following materials: polyester, polypropylene, polyethylene, nylon, viscous rayon fibers, cellulose acetate.

11. The absorbent article of claim 4 wherein the fibers in the second group of fibers comprise capillary channel fibers.

12. The absorbent article of claim 4 wherein the fibers in the second group of fibers are compression resistant.

13. The absorbent article of claims 4 or 12 wherein the fibers in the second group of fibers are wet and dry resilient.

14. The absorbent article of claim 4 wherein the fibers in the second group of fibers are greater than or equal to 0.6 cm long.

15. The absorbent article of claim 4 wherein the fibers in the second group of fibers are greater than or equal to 1.3 cm long.

16. The absorbent article of claim 4 wherein the fibers in the second group of fibers have a denier per filament of between about 4 and about 60.

17. The absorbent article of claim 4 wherein the fibers in the second group of fibers have a denier per filament of between about 15 and about 30.

18. The absorbent article of claim 4 wherein the fibers in the second group of fibers have a denier per filament of between about 15 and about 25.

19. The absorbent article of claim 1 wherein the fibers in the second group of fibers are crimped at a crimping frequency of between 5 and 7 per linear 2.5 cm.

20. The absorbent article of claim 19 wherein the fibers in the second group of fibers are crimped at a crimping angle of between about 70° to about 90°.

21. The absorbent article of claim 4 wherein said second group of fibers comprise between about 5% to about 90% of the weight of fibers in said absorbent core.

22. The absorbent article of claim 4 wherein said second group of fibers comprise between about 10% to about 90% of the weight of fibers in said absorbent core.

23. The absorbent article of claim 22 wherein said second group of fibers comprise between about 10% to about 30% of the weight of fibers in said absorbent core.

24. The absorbent article of claim 4 wherein the fibers in said second group of fibers are selected from the group consisting of one of the following: hydrophobic or partially hydrophilic and partially hydrophobic.

25. The absorbent article of claim 4 wherein said absorbent core has a density of greater than or equal to 0.09 g/cm$^3$ and less than or equal to about 0.25 g/cm$^3$.

26. The absorbent article of claim 4 wherein said absorbent core additionally comprises absorbent hydrogel-forming polymer material.

27. The absorbent article of claim 26 wherein said hydrogel-forming polymer material is capable of absorbing synthetic urine at such a rate that said polymer material reaches at least about 40% of its absorptive capacity in less than or equal to about 10 seconds.

28. The absorbent article of claims 26 or 27 wherein said absorbent, hydrogel-forming polymer material is in fibrous form.

* * * * *